(12) United States Patent
Zhong et al.

(10) Patent No.: US 8,293,963 B2
(45) Date of Patent: Oct. 23, 2012

(54) PROCESS FOR THE CRYSTALLIZATION SEPARATION OF P-XYLENE

(75) Inventors: Luping Zhong, Shanghai (CN); Jian Xiao, Shanghai (CN); Yongyan Lu, Shanghai (CN); Yanzi Guo, Shanghai (CN); Dejin Kong, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 335 days.

(21) Appl. No.: 12/623,245

(22) Filed: Nov. 20, 2009

(65) Prior Publication Data

US 2010/0137660 A1 Jun. 3, 2010

(30) Foreign Application Priority Data

Nov. 21, 2008 (CN) .......................... 2008 1 0043977

(51) Int. Cl.
*C07C 7/14* (2006.01)

(52) U.S. Cl. ......... 585/812; 585/820; 585/828; 585/471

(58) Field of Classification Search .................. None
See application file for complete search history.

(56) References Cited

U.S. PATENT DOCUMENTS

| | | | |
|---|---|---|---|
| 2,985,589 A | 5/1961 | Broughton et al. | |
| 3,177,255 A | 4/1965 | Ehrhart et al. | |
| 3,467,724 A | 9/1969 | Laurich | |
| 3,558,732 A | 1/1971 | Neuzil et al. | |
| 3,686,342 A | 8/1972 | Neuzil | |
| 3,734,974 A | 5/1973 | Neuzil | |
| 4,011,276 A * | 3/1977 | Chu | 585/471 |
| 5,284,992 A | 2/1994 | Hotier et al. | |
| 6,060,634 A * | 5/2000 | Mikitenko et al. | 585/814 |
| 2002/0107427 A1 * | 8/2002 | Doyle et al. | 585/828 |

FOREIGN PATENT DOCUMENTS

CN 98810104.1 12/2000

OTHER PUBLICATIONS

English language abstract of CN 98810104.1.

* cited by examiner

*Primary Examiner* — Tam M Nguyen
(74) *Attorney, Agent, or Firm* — Finnegan, Henderson, Farabow, Garrett & Dunner, LLP

(57) ABSTRACT

Provided is a process for crystallization separating p-xylene, comprising: a) feeding a mixed xylenes stream comprising greater than or equal to 60% by weight, of p-xylene, such as 60% to 98% by weight of p-xylene, to a crystallization unit to perform cooling crystallization, to obtain a slurry comprising p-xylene crystals; and b) feeding the slurry to a filtration and purification unit, to obtain a mother liquor, washings, and p-xylene, wherein the filtration and purification unit uses a simulated moving bed or a combination of multiple moving beds.

13 Claims, 1 Drawing Sheet

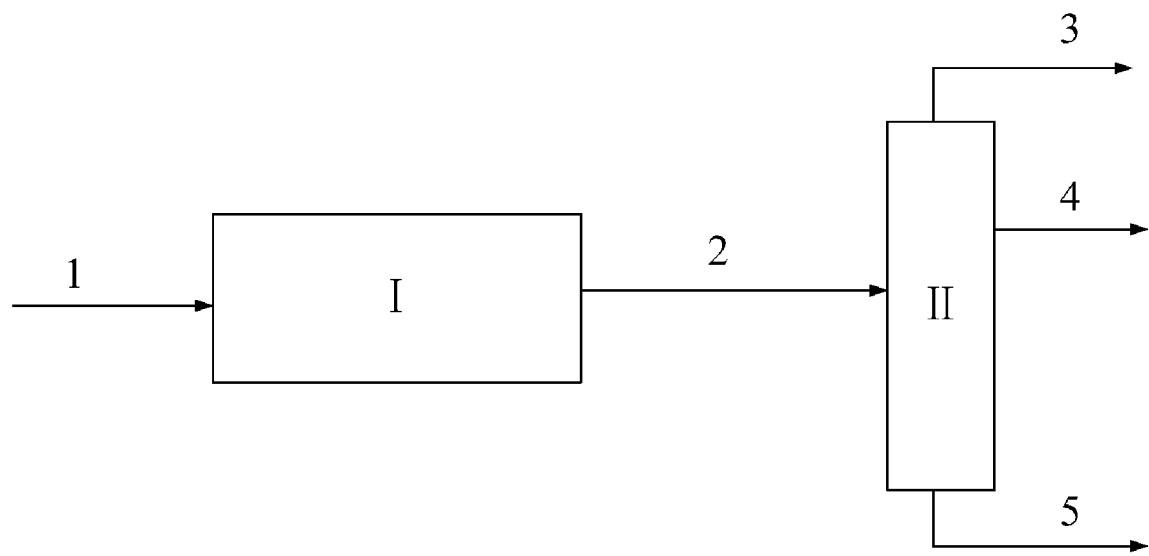

PROCESS FOR THE CRYSTALLIZATION SEPARATION OF P-XYLENE

The present application claims the benefit of Application No. CN200810043977.6, filed on Nov. 21, 2008.

Provided are processes for the crystallization separation of p-xylene.

P-xylene (PX) is one of basic organic feedstocks in petrochemical industry, and is often used in production of various chemicals, such as chemical fibers, synthetic resins, agrochemicals and medicines. P-xylene is typically produced from an ethylbenzene-containing xylene stream, i.e., $C_8$ aromatic hydrocarbons ($C_8A$) stream, in thermodynamic equilibrium derived from catalytic reforming of naphtha, wherein p-xylene may be separated from a mixture of isomers having similar boiling points using a multi-stage cryogenic crystallization separation technique or a simulated moving bed molecular sieve adsorption separation (referred to as adsorption separation) technique. The separated o- and m-xylenes are generally isomerized to form mixed xylenes including p-xylene using a $C_8A$ isomerization (referred to as isomerization) technique.

Various $C_8$ aromatic hydrocarbons have similar boiling points: for example, 136.2° C. for ethylbenzene, 138.4° C. for p-xylene, 139.1° C. for m-xylene, and 144.4° C. for o-xylene. O-xylene having the highest boiling point can be separated by rectification process, which however may require more than one hundred of theoretical plates and a relatively high reflux ratio. Ethylbenzene having the lowest boiling point can also be separated by rectification process, which however may be much more difficult than that for o-xylene. Various $C_8$ aromatic hydrocarbons have different melting points: for example, 13.3° C. for p-xylene, −25.2° C. for o-xylene, −47.9° C. for m-xylene, and −94.95° C. for ethylbenzene. P-xylene has the highest melting point, and can be separated by a crystallization process. If the concentration of p-xylene in a feedstock is not high, a two-stage crystallization process may generally be employed in order to achieve an industrially acceptable yield. Furthermore, due to the difference in selectivity of an adsorbent for various $C_8$ aromatic hydrocarbons, p-xylene can be separated by an adsorption separation process. This process has become one of the major processes for the production of p-xylene once it has been industrialized in 1970's.

Provided is a process for crystallization separation of p-xylene, comprising: a) feeding a mixed xylenes stream comprising greater than or equal to 60% by weight of p-xylene, such as ranging from 60% to 98% by weight of p-xylene, to a crystallization unit to perform cooling crystallization, to thereby obtain a slurry comprising p-xylene crystals; and b) feeding the slurry to a filtration and purification unit, to obtain a mother liquor, washings, and p-xylene, wherein the filtration and purification unit uses a simulated moving bed or a combination of multiple moving beds.

BRIEF DESCRIPTION OF DRAWINGS

FIG. 1 is a schematic depiction of the flow of an embodiment of a process described herein.

Provided is a process for crystallization separation of p-xylene, comprising:

a) feeding a mixed xylenes stream comprising greater than or equal to 60% by weight of p-xylene to a crystallization unit to perform cooling crystallization, to obtain a slurry comprising p-xylene crystals; and b) feeding the slurry to a filtration and purification unit, to obtain a mother liquor, washings, and p-xylene crystals, wherein the filtration and purification unit uses a simulated moving bed or a combination of multiple moving beds.

In some embodiments, the mixed xylenes stream, i.e., the feedstock, comprises from 60% to 98% by weight, such as from 65% to 96% by weight, and further such as from 70% to 95% by weight of p-xylene. It is understood by those skilled in the art that the mixed xylenes stream may comprise, for example, ethylbenzene in addition to the various xylenes.

In some embodiments, the mixed xylenes stream is derived from a toluene selective disproportionation reaction. Specifically, in some embodiments, toluene undergoes a selective disproportionation reaction in the presence of at least one selective disproportionation catalyst. A benzene stream and a mixed xylenes stream comprising a high concentration of p-xylene may be separated from the effluent of the selective disproportionation reaction.

In the toluene selective disproportionation reaction, any of catalysts for toluene selective disproportionation known in the art may be used. In some embodiments, the toluene selective disproportionation reaction uses a ZSM-5 molecular sieve catalyst comprising at least one entity selected from platinum, molybdenum and magnesium and oxides thereof in an amount ranging from 0.005% to 5% by weight. In some embodiments, the toluene selective disproportionation reaction uses a ZSM-5 molecular sieve catalyst comprising at least one entity chosen from platinum and its oxides in an amount ranging from 0.005% to 5% by weight.

In some embodiments, the toluene selective disproportionation reaction is conducted under the following conditions: a reaction pressure ranging from 1 to 4 MPa (absolute), a reaction temperature ranging from 300° C. to 480° C., a molar ratio of hydrogen to hydrocarbons ranging from 0.5:1 to 10:1, and a weight hourly space velocity ranging from 0.8 to 8 $hr^{-4}$.

In some embodiments, the process further comprises providing the mixed xylenes stream through toluene selective disproportionation.

In some embodiments, the crystallization of p-xylene is accomplished by suspension crystallization. In some embodiments, the crystallization of p-xylene is accomplished using a scrapping well crystallizer. In some embodiments, the crystallization of p-xylene is accomplished using a stirring crystallizer.

In some embodiments, the crystallization of p-xylene is conducted at a temperature ranging from −80° C. to 5° C., such as from −75° C. to 0° C.

In some embodiments, the p-xylene filtration and purification unit comprises a simulated moving bed or a combination of multiple moving beds, to implement continuously feeding and discharging. In some embodiments, the filtration and purification unit comprises a simulated moving bed, and the simulated moving bed implements different functions of filtration and washing by switching streams via a rotary valve. In some embodiments the simulated moving bed has a bed layer number ranging from 2 to 12, such as ranging from 3 to 10, and further such as ranging from 3 to 8. In some embodiments, the filtration and purification unit comprises a combination of multiple moving beds, and the combination of multiple moving beds implements different functions of filtration and purification by rotating the moving beds to switch streams. In some embodiments, the number of the moving beds ranges from 2 to 12, such as ranging from 3 to 10, and further such as ranging from 3 to 8. In some embodiments, the filtration and purification step, a weight ratio of a washing liquid (p-xylene) to crystals ranges from 0.05 to 0.5, such as ranging from 0.05 to 0.4, further such as ranging from 0.05 to 0.3, even further such as ranging from 0.05 to 0.2, and further such as ranging from 0.05 to 0.1.

The devices used in the crystallization separation process described herein are conventional, container-type devices.

In some embodiments, the p-xylene has a chemical purity of greater than 95%, such as greater than 98%, for example, greater than 99%, and in some embodiments, greater than 99.5%. In some embodiments, the p-xylene comprises less than 0.5% of m- and o-xylene, such as less than 0.3%, for example, less than 0.2%. In some embodiments, the p-xylene comprises less than 0.5% of ethylbenzene, such as less than 0.3%, for example, less than 0.2%, such as less than 0.1%. In some embodiments, the p-xylene does not contain a detectable amount of ethylbenzene.

In some embodiments, the yield of p-xylene produced by the methods described herein is greater than 35%, such as greater than 50%, for example, greater than 60%, such as greater than 70%. In some embodiments, the yield of p-xylene is greater than 80%.

One embodiment of the present disclosure is further described in detail by reference to the FIGURE. FIG. 1 is a flow of an embodiment of the process for crystallization separating p-xylene described herein. In FIG. 1, I is a crystallization unit, II is a filtration and purification unit, 1 is a mixed xylenes stream, 2 is a slurry stream, 3 is a mother liquor stream, 4 is a washings stream, and 5 is a stream of p-xylene.

In some embodiments, the mixed xylenes feedstock 1 is fed to the crystallization unit I, where the feedstock is crystallized at a temperature ranging from −80° C. to 5° C. in a scrapping well crystallizer or a stirring crystallizer, to form the slurry 2 consisting of p-xylene crystals and mother liquor. In some embodiments, the slurry 2 is then fed to the filtration and purification unit II, where the slurry 2 is filtered and purified by washing, to give the mother liquor stream 3, the washings stream 4, and the stream of p-xylene 5.

EXAMPLES

The following examples are given to further illustrate the disclosure, but do not impose limitation to the disclosure.

Example 1

A mixed xylenes feedstock was fed to a scrapping well crystallizer, and was crystallized at −50° C. to form a slurry. The slurry was fed to a simulated moving bed having a bed layer number of 6, where different functions of the layers of the simulated moving bed were implemented by switching streams via a rotary valve so that one bed layer served as filtration bed layer, three bed layers served as washing bed layer, one bed layer served as crystal melting bed layer, and one bed layer served as product discharging bed layer. The slurry was filtered and washed in the simulated moving bed to obtain p-xylene, with a weight ratio of a washing liquid to crystals being 0.2:1. When the operation was considered to be stable, the recovery yield of p-xylene was 68.7%, and the compositions of various streams were measured. The results are shown in Table 1 below.

TABLE 1

The compositions (% by weight) of various streams in Example 1

| Components | Feedstock | Mother liquor | Washings | p-Xylene |
| --- | --- | --- | --- | --- |
| Ethylbenzene | 5.0 | 19.3 | 5.8 | 0.0 |
| m-Xylene | 5.0 | 19.7 | 6.2 | 0.1 |
| o-Xylene | 10.0 | 38.9 | 12.6 | 0.1 |
| p-Xylene | 80.0 | 22.1 | 75.4 | 99.8 |

Example 2

A mixed xylenes feedstock was fed to a stirring crystallizer, and was crystallized at −80° C. to form a slurry. The slurry was fed to a simulated moving bed having a bed layer number of 10, where different functions of the layers of the simulated moving bed were implemented by switching streams via a rotary valve so that one bed layer served as filtration bed layer, four bed layers served as washing bed layer, three bed layers served as crystal melting bed layer, and two bed layers served as product discharging bed layer. The slurry was filtered and washed in the simulated moving bed to obtain p-xylene, with a weight ratio of a washing liquid to crystals being 0.5:1. When the operation was considered to be stable, the recovery yield of p-xylene was 45.4%, and the compositions of various streams were measured. The results are shown in Table 2 below.

TABLE 2

The compositions (% by weight) of various streams in Example 2

| Components | Feedstock | Mother liquor | Washings | p-Xylene |
| --- | --- | --- | --- | --- |
| Ethylbenzene | 15.0 | 33.5 | 14.4 | 0.1 |
| m-Xylene | 10.0 | 19.7 | 8.7 | 0.0 |
| o-Xylene | 15.0 | 34.1 | 13.4 | 0.1 |
| p-Xylene | 60.0 | 12.7 | 63.5 | 99.8 |

Example 3

A mixed xylenes feedstock was fed to a scrapping well crystallizer, and was crystallized at −25° C. to form a slurry. The slurry was fed to a simulated moving bed having a bed layer number of 8, where different functions of the layers of the simulated moving bed were implemented by switching streams via a rotary valve so that one bed layer served as filtration bed layer, three bed layers served as washing bed layer, two bed layers served as crystal melting bed layer, and two bed layers served as product discharging bed layer. The slurry was filtered and washed in the simulated moving bed to obtain p-xylene, with a weight ratio of a washing liquid to crystals being 0.05:1. When the operation was considered to be stable, the recovery yield of p-xylene was 87.2%, and the compositions of various streams were measured. The results are shown in Table 3 below.

TABLE 3

The compositions (% by weight) of various streams in Example 3

| Components | Feedstock | Mother liquor | Washings | p-Xylene |
| --- | --- | --- | --- | --- |
| Ethylbenzene | 2.0 | 20.3 | 3.7 | 0.1 |
| m-Xylene | 1.0 | 10.4 | 1.8 | 0.0 |
| o-Xylene | 2.0 | 20.7 | 3.3 | 0.1 |
| p-Xylene | 95.0 | 48.6 | 91.2 | 99.8 |

Example 4

A mixed xylenes feedstock was fed to a scrapping well crystallizer, and was crystallized at −15° C. to form a slurry. The slurry was fed to a simulated moving bed having a bed layer number of 2, where different functions of the layers of the simulated moving bed were implemented by switching streams via a rotary valve so that one bed layer served as filtration bed layer, and the other bed layer served as washing, crystal melting, and product discharging bed layer. p-Xylene was obtained, with a weight ratio of a washing liquid to crystals being 0.3:1. When the operation was considered to be stable, the recovery yield of p-xylene was 71.7%, and the compositions of various streams were measured. The results are shown in Table 4 below.

TABLE 4

The compositions (% by weight) of various streams in Example 4

| Components | Feedstock | Mother liquor | Washings | p-Xylene |
|---|---|---|---|---|
| Ethylbenzene | 5.0 | 25.7 | 2.0 | 0.1 |
| m-Xylene | 2.0 | 9.4 | 0.6 | 0.0 |
| o-Xylene | 3.0 | 16.3 | 0.9 | 0.1 |
| p-Xylene | 90.0 | 48.6 | 96.5 | 99.8 |

Example 5

A mixed xylenes feedstock was fed to a scrapping well crystallizer, and was crystallized at −10° C. to form a slurry. The slurry was fed to a filtration and purification unit consisting of six moving beds, where different functions of the moving beds were implemented by rotating the moving beds so that one bed served as filtration bed, three beds served as washing bed, one bed served as crystal melting bed, and one bed served as product discharging bed. Filtration, washing, crystal melting, and product discharging were conducted in the moving beds to give p-xylene, with a weight ratio of a washing liquid to crystals being 0.2:1. When the operation was considered to be stable, the recovery yield of p-xylene was 61.8%, and the compositions of various streams were measured. The results are shown in Table 5 below.

TABLE 5

The compositions (% by weight) of various streams in Example 5

| Components | Feedstock | Mother liquor | Washings | p-Xylene |
|---|---|---|---|---|
| Ethylbenzene | 5.0 | 11.2 | 5.8 | 0.0 |
| m-Xylene | 5.0 | 11.2 | 6.2 | 0.1 |
| o-Xylene | 5.0 | 22.3 | 14.2 | 0.1 |
| p-Xylene | 85.0 | 55.3 | 73.8 | 99.8 |

Example 6

A mixed xylenes feedstock was fed to a stirring crystallizer, and was crystallized at −80° C. to form a slurry. The slurry was fed to a filtration and purification unit consisting of eleven moving beds, where different functions of the moving beds were implemented by rotating the moving beds so that one bed served as filtration bed, five beds served as washing bed, three beds served as crystal melting bed, and two beds served as product discharging bed. Filtration, washing, crystal melting, and product discharging were conducted in the moving beds to give p-xylene, with a weight ratio of a washing liquid to crystals being 0.5:1. When the operation was considered to be stable, the recovery yield of p-xylene was 38.1%, and the compositions of various streams were measured. The results are shown in Table 6 below.

TABLE 6

The compositions (% by weight) of various streams in Example 6

| Components | Feedstock | Mother liquor | Washings | p-Xylene |
|---|---|---|---|---|
| Ethylbenzene | 15.0 | 34.5 | 13.2 | 0.1 |
| m-Xylene | 10.0 | 19.7 | 7.9 | 0.0 |
| o-Xylene | 15.0 | 33.4 | 12.1 | 0.1 |
| p-Xylene | 60.0 | 12.4 | 66.8 | 99.8 |

Example 7

A mixed xylenes feedstock was fed to a scrapping well crystallizer, and was crystallized at 5° C. to form a slurry. The slurry was fed to a filtration and purification unit consisting of eight moving beds, where different functions of the moving beds were implemented by rotating the moving beds so that one bed served as filtration bed, three beds served as washing bed, two beds served as crystal melting bed, and two beds served as product discharging bed. Filtration, washing, crystal melting, and product discharging were conducted in the moving beds to give p-xylene, with a weight ratio of a washing liquid to crystals being 0.05:1. When the operation was considered to be stable, the recovery yield of p-xylene was 72.3%, and the compositions of various streams were measured. The results are shown in Table 7 below.

TABLE 7

The compositions (% by weight) of various streams in Example 7

| Components | Feedstock | Mother liquor | Washings | p-Xylene |
|---|---|---|---|---|
| Ethylbenzene | 2.0 | 7.4 | 3.9 | 0.1 |
| m-Xylene | 1.0 | 3.5 | 2.1 | 0.0 |
| o-Xylene | 2.0 | 8.5 | 4.3 | 0.1 |
| p-Xylene | 95.0 | 80.4 | 89.7 | 99.8 |

Example 8

A mixed xylenes feedstock was fed to a scrapping well crystallizer, and was crystallized at −80° C. to form a slurry. The slurry was fed to a filtration and purification unit consisting of two moving beds, where different functions of the moving beds were implemented by rotating the moving beds so that one bed served as filtration bed, and the other bed served as washing, crystal melting, and product discharging bed. Filtration, washing, crystal melting, and product discharging were conducted in the moving beds to give p-xylene, with a weight ratio of a washing liquid to crystals being 0.3:1. When the operation was considered to be stable, the recovery yield of p-xylene was 86.4%, and the compositions of various streams were measured. The results are shown in Table 8 below.

TABLE 8

The compositions (% by weight) of various streams in Example 8

| Components | Feedstock | Mother liquor | Washings | p-Xylene |
|---|---|---|---|---|
| Ethylbenzene | 5.0 | 43.7 | 2.5 | 0.1 |
| m-Xylene | 2.0 | 26.2 | 0.8 | 0.0 |
| o-Xylene | 3.0 | 17.7 | 1.3 | 0.1 |
| p-Xylene | 90.0 | 12.6 | 95.4 | 99.8 |

What is claimed is:

1. A process for crystallization separation of p-xylene, comprising:
   a) feeding a mixed xylenes stream comprising greater than or equal to 60% by weight of p-xylene to a crystallization unit to perform cooling crystallization, to obtain a slurry comprising p-xylene crystals; and
   b) feeding the slurry to a filtration and purification unit, to obtain a mother liquor, washings, and p-xylene crystals, wherein the filtration and purification unit uses a simulated moving bed or a combination of multiple moving beds to conduct the filtration and purification of the slurry comprising p-xylene crystals.

2. The process of claim 1, wherein in step a), suspension crystallization is used for the crystallization of p-xylene.

3. The process of claim 1, wherein the crystallization unit is a scrapping well crystallizer or a stirring crystallizer.

4. The process of claim 1, wherein the crystallization of p-xylene is conducted at a temperature ranging from −80° C. to 5° C.

5. The process of claim 1, wherein the filtration and purification unit employs a simulated moving bed, where the different functions of filtration and washing are implemented by switching streams via at least one rotary valve.

6. The process of claim 5, wherein the simulated moving bed has a layer number ranging from 2 to 12.

7. The process of claim 1, wherein the filtration and purification unit employs a combination of multiple moving beds, where the different functions of filtration and purification are implemented by rotating the moving beds to switch streams.

8. The process of claim 7, wherein the number of the moving beds ranges from 2 to 12.

9. The process of claim 1, wherein in the filtration and purification, a weight ratio of a washing liquid to p-xylene crystals ranges from 0.05:1 to 0.5:1.

10. The process of claim 1, wherein the mixed xylenes stream is obtained through toluene selective disproportionation.

11. The process of claim 10, wherein the toluene selective disproportionation uses a ZSM-5 molecular sieve catalyst comprising at least one entity selected from platinum, molybdenum and magnesium and oxides thereof.

12. The process of claim 11, wherein the ZSM-5 molecular sieve catalyst is in an amount ranging from 0.005% to 5% by weight.

13. The process of claim 11, wherein the toluene selective disproportionation is conducted under at least one of the following conditions: a reaction pressure ranging from 1 to 4 MPa, a reaction temperature ranging from 300 to 480° C., a molar ratio of hydrogen to hydrocarbons ranging from 0.5:1 to 10:1, and a weight hourly space velocity ranging from 0.8 to 8 $hr^{-1}$.

* * * * *